US00PP21141P3

(12) United States Plant Patent
Maillard et al.

(10) Patent No.: US PP21,141 P3
(45) Date of Patent: Jul. 6, 2010

(54) NECTARINE TREE NAMED 'NECTATOP'
(50) Latin Name: ***Prunus persica* var. nucipersica**
Varietal Denomination: Nectatop

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/382,090

(22) Filed: Mar. 9, 2009

(65) Prior Publication Data

US 2009/0235404 P1 Sep. 17, 2009

(30) Foreign Application Priority Data

Mar. 17, 2008 (QZ) ..... PBR 2008/0578

(51) Int. Cl.
*A01H 5/00* (2006.01)

(52) U.S. Cl. ..... Plt./190

(58) Field of Classification Search ..... Plt./190
See application file for complete search history.

*Primary Examiner*—Annette H Para
(74) *Attorney, Agent, or Firm*—Westerman, Hattori, Daniels & Adrian, LLP

(57) ABSTRACT

A new and distinct variety of nectarine tree, denominated 'Nectatop', has fruits of very long shelf life withour alteration before and after harvesting, a semi-sweet yellow flesh of high-eating quality and an attractive red skin. Fruits can be consumed crunchy or melting.

3 Drawing Sheets

Botanical classification: *Prunus persica* var. *nucipersica*.
Variety denomination: 'Nectatop'.

BACKGROUND OF THE VARIETY

The present invention relates to a new and distinct variety of *Prunus persica* var. *nucipersica* yellow nectarine tree, which has been given the denomination 'Nectatop'. This tree, named 'Nectatop', produces clingstone fruits of good eating quality for fresh market in early August in the 66—Pyrénées-Orientales departement—France. Contrast is made to 'Nectapink' (U.S. Plant Pat. No. 17,584), 'Nectaross' (non-patented), 'Maillardou' (Bonbon®) (non-patented) and 'Maillarboom' (Big Bourn®) (non-patented) yellow nectarine trees, standard varieties, for reliable description. 'Nectatop' is a promising candidate for commercial success in that it has an evenness of maturity, and produces regular fruits in large quantity and with a high productivity. It was chosen because of its hardiness and fruit lifetime before and after harvest, and because of its aromatic semi sweet taste.

ORIGIN OF THE VARIETY

'Nectatop' nectarine tree originated in a cultivated area of the south of France, in the 66—Pyrénées-Orientales departement—France where it was tested. This place is under a Mediterranean climate in a temperate area characterized by irregular and low precipitation with drought in summer, high temperatures all year long. The 'Nectatop' variety was obtained by seedling. The male parent was 'Maillardou' (Bonbon®) (non-patented) yellow nectarine tree and the female parent was 'Maillarboom' (Big Bourn®) (non-patented) yellow nectarine tree. 'Nectatop' was provisionally designated, tested and genetically identified by a genetic profile, as 03.22.87 NJ and was registered at the Official Catalogue of the Agriculture Ministry of the French Republic on Nov. 14, 2007 under number 1024463. It was obtained by hybridizing and propagated by grafting on a 'Franc Inra Montclar®' (non-patented) rootstock tree. It has been determined to have unique tree and fruit characteristics making it worthy for commercial fresh fruit production. There are no known effects of the standard 'Franc Inra Montclar®' (non-patented) rootstock on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France.

SUMMARY OF THE VARIETY

The new and distinct variety of nectarine tree blooms in March at Perpignan in the Pyrénées-Orientales departement, France. More particularly, it generally blooms between March 7$^{th}$ and March 20$^{th}$, approximately 3 days after 'Nectaross' (non-patented) and 5 days after 'Nectapink' (U.S. Plant Pat. No. 17,584).

The first fruit of 'Nectatop' ripens in early August, 4 days after 'Nectapink' (U.S. Plant Pat. No. 17,584). More particularly, it approximately ripens between August 1$^{st}$ and August 10$^{th}$. 'Nectatop' also ripens 17 days after 'Maillarboom' and 27 days before 'Maillardou'.

DESCRIPTION OF THE DRAWINGS

In the accompanying drawing, which are as nearly true as it is reasonably possible to make in a color illustration of this type.

DETAILED BOTANICAL DESCRIPTION

Figure 1:
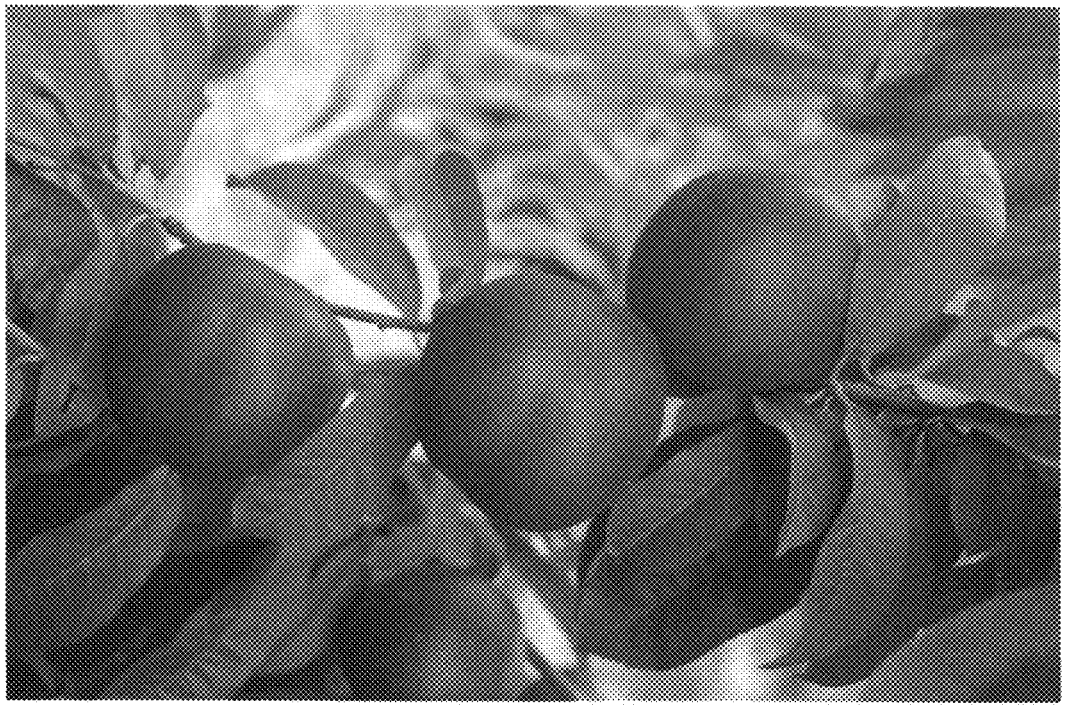
FIG. 1 is a color photograph which shows a twig bearing typical fruit specimens of the new variety, and leaves of the new variety.
Figure 2:
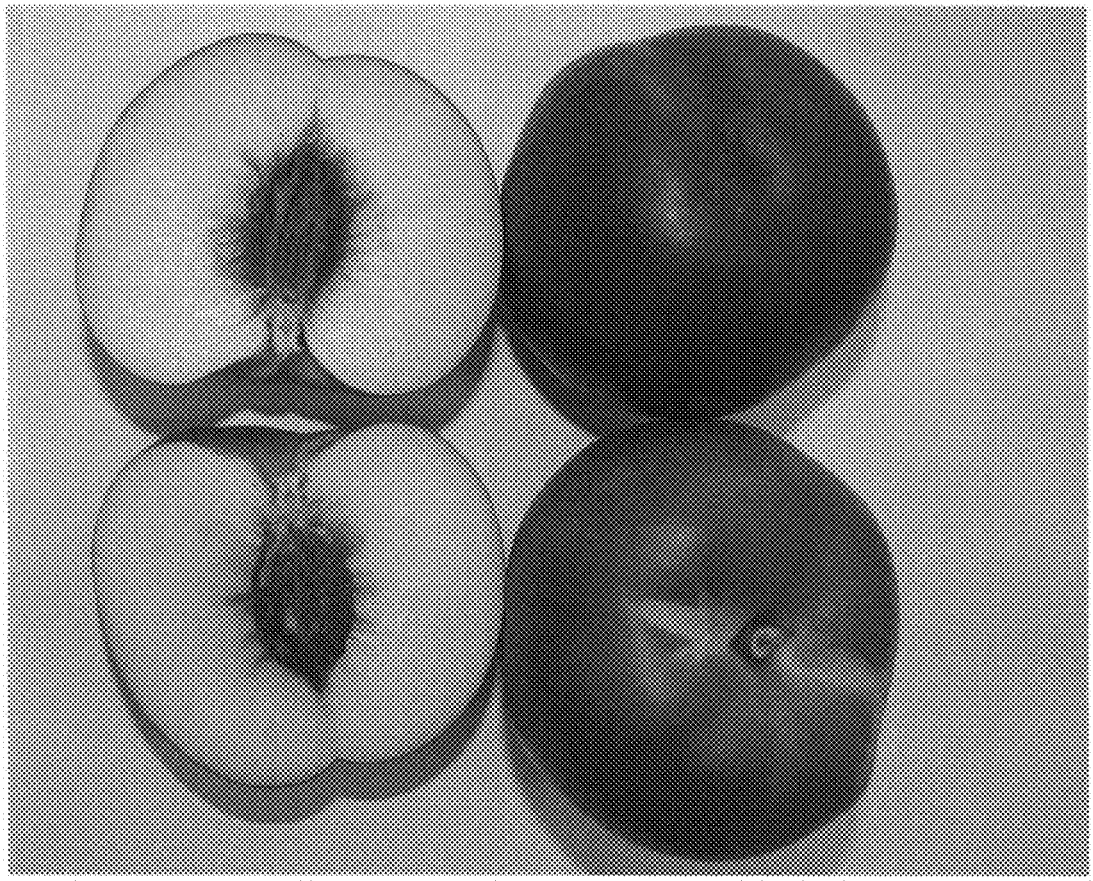
FIG. 2 is a color photograph which shows two whole fruit sufficiently mature for harvesting and shipment, and a third fruit cut in half with the pit left in one of the halves for depicting the fruit flesh, the pit cavity and the stone of the new variety.
Figure 3:
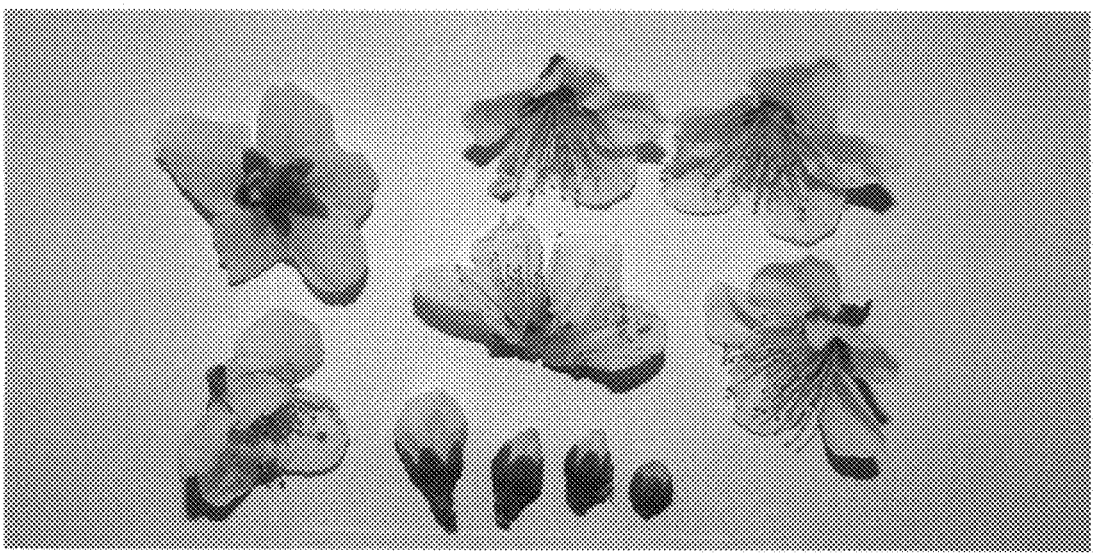
FIG. 3 is a color photograph with reverse and size views of flowers of the new variety, and, with petals removed, reproductive organs of the new variety.

The tree, flowers, and fruit may vary in slight detail due to variations in soil type, cultural practices, and climatic condition.

Trees are vigorous and of medium stature, half-standing in a semi-spread to semi-upright out aspect. The anthocyanic coloration of the flowering shoot is present excluding brushwood side away from sun. Flowering begins semi-early in springtime. The type of flower is showy with medium to large pink petals. Leaf glands are present and reniform. Time of maturity for consumption is semi-late. The fruit flesh is yellow with slight red pigmentation around stone cavity. Fruit skin color features an homogeneous dark red blush. Fruit taste is semi-sweet.

The 'Nectatop' variety blooms approximately 5 days after 'Nectapink' (U.S. Plant Pat. No. 17,584) and has a similar amount of flowers per meter. The first fruit of 'Nectatop' ripens 4 days after 'Nectapink' (U.S. Plant Pat. No. 17,584). 'Nectatop' fruits are more rounded and have a more attractive skin than 'Nectapink' fruits, the skin blush color being more intense and luminous.

The 'Nectatop' variety blooms approximately 3 days after 'Nectaross' (non-patented) and 'Nectatop' fruits are semi-sweet instead of acidulated for 'Nectaross' fruits.

The new variety female parent, which is 'Maillarboom' (Big Boom®) (non-patented), comparatively ripens 17 days earlier than the new variety, has fruits of similar size but produces less pollen, the pollen also being of less quality.

The new variety male parent, which is 'Maillardou' (Bonbon®) (non-patented), comparatively ripens 27 days later than the new variety. 'Maillardou' produces fruits of medium size but very tasty, thus rendering this variety interesting as a genitor. 'Maillardou' trees also have more flowers than the new variety.

DETAILED DESCRIPTION

Referring more specifically to the pomological details of this new and distinct variety of nectarine tree, the following was observed during the 2007 and 2008 growing seasons under the ecological conditions prevailing at the orchards located near the town of Elne, Pyrénées-Orientales departement, France. All observations have been done on rootstock cultivar. The rootstock was a 'Franc Inra Montclar®' (non-patented) tree. More particularly, observations relative to tree, trunk, branches, leaves and fruit were done in August 2007 and August 2008 on trees in their fourth and fifth growing season. Observations relative to flowers were done in March 2007 and March 2008 on trees in their fourth and fifth growing season. All major color code designations are by reference to The R.H.S. Color Chart (Fourth Edition) provided by The Royal Horticultural Society of Great Britain.

TREE

Size:

*Generally.*—Considered large. The tree size the first year was approximately 280 cm. The tree was pruned during each following dormant season to a height of approximately 250 cm. Current season shoots growth could reach 80 cm. The tree size from the second year (second and next years) reached a final height of 330 cm with current season shoots length comprised.

Spread: Approximately 150 to 200 cm with a cylindrical shape. The whole orchard was oriented to a central leader organization, with tree lines spaced of 4.0 meters and trees spaced of 1.0 meter in a same tree line. As a result, the orchard contains 2500 trees by hectare.

Vigour: Considered vigorous (Trees height ranges from 200 cm to 280 cm).

Productivity: Very productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

Bearer: Very regular. Fruit set has been heavy during the years of observation and thinning of 1 fruit on 3 was necessary every year.

Form: The 'Nectatop' variety has naturally a semi-spread to semi-upright shape.

Density: Considered dense.

Hardiness: The present tree was grown and evaluated in France. The variety appeared to be hardy under typical central Pyrénées-Orientales departement climatic conditions. Experimentations on different sites with winter chilling requirement comprised between 350 and 1200 hours showed a good behavior of the tree in all cases. Ascertained temperatures as low as −12 degrees Celsius caused no damages to the tree. The tree was also very resistant to frosty springtime weather.

TRUNK

Diameter: Approximately between 8.0 and 9.0 cm in diameter when measured at a distance of approximately 30 cm above the soil level.

Bark texture: Considered rough.

Lenticels: Numerous lenticels are present. The lenticels range in size from approximately 0.5 to 0.9 cm in width, and from 0.2 to 0.3 cm in height.

Lenticel color: The outside of lenticels has a silver-grey color (varying from RHS Grey 201 D to RHS Black 202 D), whereas the inside is considered brown (RHS Greyed Orange 166 B).

Bark coloration: The bark has a silver-grey color (varying from RHS Grey 201 C to RHS Black 202 C)

BRANCHES

Size: Mature branches as well as current season shoots are medium to thick for the variety.

Diameter: Average as compared to other nectarine varieties. The current season shoots have a diameter from 6.0 to 9.0 millimeters, and branches of trees have a diameter comprised between 23.0 and 33.0 millimeters.

Surface texture: Average, several years old wood has no furrowed appearance.

Crotch angles: Primary branches are considered variable, but the crotch angles are generally between 50 and 60 degrees from the horizontal axis. This particular characteristic is not considered distinctive of the variety, however.

Current season shoots:

*Surface texture.*—Substantially glabrous.

Internode length: Generally 22.0 to 30.0 millimeters.

Color of mature branches: Medium brown (RHS Grey Brown 199 A).

Current seasons shoots:

*Color.*—The color of new shoot tips is considered a light yellow green (varying from RHS Yellow Green 144 A to RHS Yellow Green 144 B) on lower part of new shoot tips, whereas the upper part is colored in orange brown (varying from RHS Greyed Orange 173 B to RHS Greyed Orange 173 C).

LEAVES

Size: Considered medium to large for the species. Leaf measurements have been taken from vigorous, upright, current-season growth at approximately mid-shoot. The ratio leaf length/leaf width is around 3,90.

Leaf length: Approximately 175 to 200 millimeters with petiole.

Leaf width: Approximately 41 to 51 millimeters

Leaf base shape: Concave.

Leaf form: Lanceolate.

Leaf tip form: Small and acuminate

Leaf color:

*Upper leaf surface.*—Dark Green (RHS Green 137 A).

*Lower surface.*—Medium Green (RHS Green 137 B to 137 C).

Leaf texture: Smooth and glabrous.

Leaf venation: Pinnately veined.

Mid-vein:

*Color.*—Light yellow green (RHS Yellow Green 144 D to 144 C).

Leaf margins: Slightly undulating.

Form: Considered slightly dentate.

Uniformity: Leaves are isolated or grouped by 2 or 3. In this last case, it is found one leaf of normal size with one or two smaller leaves (size-reduction of 50% and more).

Leaf petioles:

*Size.*—Considered medium.

*Length.*—Between 9.0 and 12.0 mm.

*Diameter.*—About 2.5 mm.

*Color.*—Light yellow green (RHS Yellow Green 144 D to 144 C).

Leaf glands:

*Size.*—Considered medium.

*Number.*—2 to 4 glands on the leaf, although 3 glands are most generally observed.

*Type.*—Reniform.

*Color.*—On young leaves, leaf glands color is considered a pale green (RHS Green 144 B). On older leaves, leaf glands color turn to a dark brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variables dimensions. Just before blooming, floral buds are approximately 10.0 millimeters wide and approximately 18.0 millimeters long.

Flower buds:

*Color.*—This characteristic is dependent upon the proximity to bloom. At pre-floral stage of development, the bottom of the flowers buds, formed by sepals, is of purple-brown color (RHS Greyed Purple 183 A); the corolla, formed by petals, is generally of pale pink color (varying from RHS Red Purple 65 B to RHS Red Purple 69C). Petals color shows an evolution until the end of flowering. The buds are considered hardy under typical central Pyrénées-Orientales departement climatic conditions.

Hardiness: No winter injury was noted during the last several years of evaluation in the central Pyrénées Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally early March. The first bloom was observed on Mar. 6, 2004.

Blooming time: Considered middle season in relative comparison to other commercial nectarine cultivars grown in the Pyrénées-Orientales departement, France. The date of full bloom is observed on March, more particularly between March $7^{th}$ and March $20^{th}$. The date of bloom varies slightly with climatic conditions and cultural practices.

Duration of bloom: Approximately between 10 and 14 days. This characteristic varies slightly with the prevailing climatic conditions.

Flower type: The variety is considered to have showy type flowers.

Flower size: Considered medium. Flower diameter at full bloom is approximately between 30.0 to 40.0 millimeters.

Bloom quantity: Considered abundant, approximately between 40 and 45 flowers per meter.

Flower bud frequency: Generally 2 flower buds appear per node, occasionally 1.

Petal size:

*Generally.*—Considered medium to large for the species.

Length: Generally about 19.0 millimeters.

Width: Generally about 18.0 millimeters.

Petal form: Rounded.

Petal count: Nearly always 5.

Petal texture: Smooth and glabrous.

Petal color: Light Pink (RHS Red Purple 69 B to C) to Medium Pink (RHS Red Purple 65 B to C), slightly darkening with senescence.

Fragrance: Pronounced.

Petal claw:

*Form.*—The claw is considered to have a conic form with a slighty rounded extremity.

*Length.*—Approximately between 6.0 and 8.0 millimeters.

*Width.*—Approximately between 5.0 and 6.0 millimeters.

Petal margins: Generally slightly undulated.

Petal apex:

*Generally.*—The petal apices have a large dome-shaped form.

Flower pedicel:

*Length.*—Considered medium-long and having an average length of approximately 3.0 to 5.0 millimeters.

*Diameter.*—Approximately 2.0 millimeters.

*Color.*—A medium brown (RHS Grey Brown N199 B to 199 C).

Floral nectaries:
*Color.*—A flat golden orange (approximately RHS Greyed Red 178 C to B).
Calyx:
*Internal surface texture.*—Smooth and glabrous.
*Color.*—The outer surface of the calyx is considered of Purple-brown (RHS Greyed Purple 183 A) color.
Sepals:
*Surface texture.*—The outer surface has a fine pubescent texture.
*Size.*—Generally medium.
*Color.*—A Brown Purple (RHS Greyed Purple 183 A).
Average number of stamens per flower: About 40 stamens per flower.
Anthers:
*Generally.*—Small to medium in length.
*Color.*—Red to orange-red color (approximately RHS Greyed Purple 178 A). Anthers are becoming yellow at maturity.
Pollen production: Pollen is abundant, and has a yellow color (Approximately RHS Yellow Orange 17 B to C). The present variety is considered self fruitful (self-pollinating).
Filaments:
*Size.*—Variable in length, approximately 9.0 to 15.0 millimeters in length. Length is generally superior or equal to pistil's length.
Color: Considered light to medium pink (varying from RHS Red Purple 62 C–D to Red Purple 73 A–B).
Pistil:
*Number.*—Usually 1.
*Generally.*—Medium in size.
*Length.*—Approximately 16.0 to 20.0 millimeters including the ovary; Generally smaller or equal to filament's length.
*Color.*—Considered a very pale green (varying from RHS Yellow Green 150 D Group to RHS Yellow Green 151 D Group).
*Surface texture.*—The variety has a glabrous pistil.

FRUIT

Maturity when described: Very firm ripe condition (shipping ripe).
Date of first picking: Aug. 14, 2004. However, the picking generally occurs between August 1$^{st}$ and August 10$^{th}$ under normal climatic conditions. The date of harvest varies slightly with the prevailing climatic conditions.
Date of last picking: Aug. 25, 2004. Only 2 harvests in 10 days were necessary.
Size:
*Generally.*—Considered large, and uniform.
Average cheek diameter: Approximately 75.0 to 80.0 millimeters.
Average axial diameter: Approximately 67.0 to 75.0 millimeters
Typical weight: Approximately between 200.0 and 260.0 grams. This characteristic is high dependent upon the prevailing cultural practices, and therefore is not particularly distinctive of the variety.
Fruit form:
*Generally.*—Round to slightly flat. The fruit is generally uniform in symmetry, viewed from pistil end.
Fruit suture: Very shallow and smooth, extending from the base to the apex. No apparent callousing or stitching exists along the suture line.
Suture:
*Color.*—This has generally a color similar to the whole fruit color, a bright dark red (RHS Greyed Purple 185 A).
Ventral surface:
*Form.*—Smooth.
Apex: Non-prominent, slightly depressed, very small.
Base: Shallow.
Stem cavity: Average depth of the stem cavity is about 1.0 cm. Average width is about 1.7 cm.
Fruit skin:
*Thickness.*—Considered very thick and strong, and very tenacious to the flesh to tenacious to the flesh depending on stage of maturity.
*Texture.*—Glabrous.
*Taste.*—Semi-sweet with a high sugar level.
*Tendency to crack.*—None observed.
Color:
*Blush color.*—This blush color is generally a dark red (RHS Greyed Purple 185 A) covering 90% to 100% of the fruit skin surface.
*Ground color.*—Orange-Red (RHS Orange Red N 34 A to RHS Orange Red 34 B).
Fruit stem: Medium in length, approximately 6.0 millimeters.
Diameter: Approximately 4.0 millimeters.
Color: Pale green (RHS Yellow Green 145A to 145 B).
Flesh:
*Ripens.*—Very evenly, homogenous, long shelf-life of the fruit.
*Texture.*—Very firm, very dense, juicy at harvest maturity stage.
*Fibers.*—No fibers.
*Aroma.*—Pronounced.
*Eating quality.*—Considered very good and aromatic.
*Flavor.*—Considered semi-sweet. The Brix is generally superior to 13.0 degrees. Acidity is comprised between 5 and 9 meq/100ml. The flavor is considered aromatic. The flesh is juicy.
*Juice.*—Very juicy at complete maturity.
*Brix.*—Generally superior to 13.0 degrees. This characteristic varies slightly with the number of fruit per tree, the prevailing cultural practices and the surrounding climatic conditions.
*Flesh color.*—Generally Yellow Orange (RHS Yellow Orange 16 B) with a slight star-shaped red pigmentation around the stone (RHS Red 45 A to B).

STONE

Type: Clingstone.
Size: Considered medium for the variety.
Length: Approximately 34.0 to 38.0 millimeters.
Width: Approximately 26.0 to 28.0 millimeters.
Diameter: Approximately 18.0 to 20.0 millimeters.
Form: Elliptic.
Base: Straight.
Apex:
*Shape.*—The stone apex has a small sharp tip.
Stone cavity: Considered medium size, with an elliptic-form and dimensions corresponding to stone's dimensions.
Stone surface:
*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

Ventral edge:

*Width.*—Considered small to medium, and having a dimension of approximately 2.0 millimeters at mid-suture.

Dorsal edge:

*Shape.*—Grooved.

Stone color: The color of the dry stone is generally a light orange-brown (RHS Greyed Orange 176 D) with some occurrences of red-brown (RHS Greyed Red 178 B).

Tendency to split: Splitting is absent.

Kernel:

*Size.*—The kernel is considered medium.

*Length.*—About 20.0 millimeters.

*Width.*—About 12.0 millimeters.

*Thickness.*—About 3.0 to 4.0 millimeters.

*Form.*—Considered elliptic.

*Pellicle.*—Pubescent.

*Color.*—The kernel skin is brown-orange (RHS Greyed Orange 167 C) with darker brown-orange streaks (RHS Greyen Orange 166 C). The almond is cream-white (RHS Orange Chite 159 D). The kernel and its embryo are mature at the time of fruit maturity.

Use: The subject variety 'Nectatop' is considered to be a nectarine tree of the semi-late season of maturity, and which produces fruits that are considered very firm, attractively colored. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping.

Keeping quality: Excellent. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

Shipping quality: Considered very good. Fruits of the new nectarine variety showed minimal bruising of the flesh or skin damage after being subjected to normal harvesting and packing procedures. Its resistance to handling during harvest and packing and its long shelf life without alteration after harvest easily permit 3 to 4 weeks shipping at 2 degrees Celsius.

Resistance to insects and disease: No particular susceptibilities were noted. Under our climatic conditions, favourable to powdery mildew, and with few treatments, the present variety has not been shown to be very sensitive to powdery mildew, or conservation diseases and decay due to its thick and strong skin. No bacteriostatic substances were applied, and no symptom was observed.

Although the new variety of nectarine tree possesses the described characteristics when grown under the ecological conditions prevailing near the town of Elne, France, it should be understood that variations of the usual magnitude and characteristics incident to changes in growing conditions, fertilization, pruning, pest control and horticultural management are to be expected.

We claim:

1. A new and distinct variety of nectarine tree as illustrated and described, characterized by fruits of very long shelf life without alteration before and after harvesting, with a semi-sweet yellow flesh of high eating quality and an attractive skin, with a very high percentage of red blush.

* * * * *